United States Patent
Blanchard et al.

(10) Patent No.: US 11,020,276 B1
(45) Date of Patent: *Jun. 1, 2021

(54) PROTECTIVE EYEWEAR

(71) Applicant: 100% Speedlab, LLC, San Diego, CA (US)

(72) Inventors: Marc Blanchard, Solana Beach, CA (US); Ludovic Boinnard, San Diego, CA (US); Jerome Jacques Marie Mage, Los Angeles, CA (US)

(73) Assignee: 100% Speedlab, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/176,674

(22) Filed: Feb. 16, 2021

Related U.S. Application Data (63) Continuation of application No. 17/071,840, filed on Oct. 15, 2020, now Pat. No. 10,918,524, which is a continuation of application No. 16/933,793, filed on Jul. 20, 2020, which is a continuation of application No. 14/548,217, filed on Nov. 19, 2014, now Pat. No. 10,716,708, which is a continuation-in-part of application No. 29/501,895, filed on Sep. 9, 2014, now Pat. No. Des. 727,400, and a continuation-in-part of application No. 13/750,093, filed on Jan. 25, 2013, now Pat. No. 10,751,218.

(60) Provisional application No. 62/048,253, filed on Sep. 9, 2014.

(51) Int. Cl.
*G02C 5/00* (2006.01)
*A61F 9/02* (2006.01)

(52) U.S. Cl.
CPC .............. *A61F 9/028* (2013.01); *G02C 5/008* (2013.01)

(58) Field of Classification Search
CPC .......... A61F 9/025; A61F 9/026; A61F 9/028; G02C 5/008; G02C 5/10; G02C 1/04; C02C 1/06
See application file for complete search history.

(56) References Cited

U.S. PATENT DOCUMENTS

| 5,760,868 A * | 6/1998 | Jannard ..................... A61F 9/02 16/228 |
| 6,029,271 A * | 2/2000 | Banuchi ..................... A61F 9/04 2/12 |
| 6,227,664 B1 * | 5/2001 | Pavlak ..................... A61F 9/026 2/437 |
| 10,716,708 B2 * | 7/2020 | Blanchard .............. G02C 5/008 |
| 10,918,524 B1 * | 2/2021 | Blanchard .............. G02C 5/008 |
| 2005/0179856 A1 * | 8/2005 | Van Atta .................. G02C 5/12 351/62 |
| 2008/0165319 A1 * | 7/2008 | Wang ..................... G02C 5/126 351/132 |
| 2013/0185849 A1 * | 7/2013 | Laughlin ................. A61F 9/025 2/431 |

(Continued)

*Primary Examiner* — Tajash D Patel
(74) *Attorney, Agent, or Firm* — Kolitch Romano LLP (57) ABSTRACT

Protective eyewear may include an eyewear frame including a left segment extending from a left pivotable temple and a right segment extending from a right pivotable temple. A lens is coupled directly to lower edges of the left and right segments, and the lens is configured to cover both eyes of a user when worn. An uppermost profile of the eyewear includes a discrete central raised portion extending upward from the left and right segments of the frame.

18 Claims, 11 Drawing Sheets

(56) References Cited

U.S. PATENT DOCUMENTS

| | | | |
|---|---|---|---|
| 2014/0059747 A1* | 3/2014 | Belbey | G02C 5/12 2/431 |
| 2014/0157496 A1* | 6/2014 | Ginther | A61F 9/029 2/439 |
| 2017/0100287 A1* | 4/2017 | Calilung | A61F 9/025 |
| 2018/0252938 A1* | 9/2018 | Thorsell | G02C 5/10 |
| 2019/0307609 A1* | 10/2019 | Young | A61F 9/028 |

* cited by examiner

PROTECTIVE EYEWEAR

CROSS-REFERENCES

The following applications and materials are incorporated herein, in their entireties, for all purposes: U.S. Provisional patent Application No. 62/048,253, filed Sep. 9, 2014 and entitled "Protective Eyewear Systems and Methods;" U.S. patent application Ser. No. 14/548,217, filed Nov. 19, 2014 and entitled "Protective Eyewear Systems and Methods;" U.S. Design patent application No. 29/501,895, filed Sep. 9, 2014, now U.S. Pat. No. D727,400, issued Apr. 21, 2015 entitled "Sunglasses;" and U.S. patent application Ser. No. 13/750,093, filed Jan. 25, 2013 and entitled "Air Cooled Goggle."

FIELD

This disclosure relates to systems and methods for eyewear. More specifically, disclosed embodiments relate to protective eyewear including glasses and goggles.

INTRODUCTION

Protective eyewear (e.g., goggles, sunglasses, and/or other eye protection devices) are used for a wide range of activities including motorcycle racing, snowboarding, skiing, BMX, road bicycling, and other activities where eye protection is critical while maintaining good visibility in a wide range of weather conditions. Increasingly complex frames have been developed to create improved fit and flex characteristics and to allow the eyewear to be used with a variety of different types of helmets. Attempts have also been made to manage airflow to prevent fogging by providing smooth, laminar airflow across the back surface of the lens. However, while protective eyewear may be used in a wide range of weather conditions, one drawback to the use of conventional eyewear is the prevention of natural air cooling. Moreover, conventional frame designs often detrimentally restrict the user's view, which can be particularly hazardous during training and sporting events. Thus, there is a need for an improved methodology for eye protection devices that provide increased viewing areas and disburse fresh air across areas where the eyewear otherwise prevents effective cooling without introducing dust or other irritants into the eyes.

SUMMARY

Techniques are disclosed for systems and methods to provide an eye protection device with an extended vertical view, among other features. An eye protection device of the present disclosure may include a frame having an outer surface that is oriented away from a user's face and an inner surface that is oriented towards the user's face. The frame may include left and right temples configured to secure the eye protection device to the user and a central raised portion disposed between a left portion and a right portion of a top portion of the frame. The central raised portion may extend vertically above a substantially continuous profile of the left and right portions to provide an extended vertical view.

In some embodiments, protective eyewear may include: an eyewear frame including a left segment extending from a left pivotable temple and a right segment extending from a right pivotable temple; and a lens coupled directly to lower edges of the left and right segments, the lens being unitary from a left side to a right side of a nose bridge of the eyewear, such that the lens is configured to cover both eyes of a user when worn; wherein an uppermost profile of the eyewear includes a discrete central raised portion extending upward from the left and right segments of the frame.

In some embodiments, protective eyewear may include: a frame and a lens collectively forming a topmost edge of the eyewear extending from a left pivotable temple to a right pivotable temple; wherein the lens is unitary from a left side to a right side of a nose bridge of the eyewear, such that the lens is configured to cover both eyes of a user when worn; and wherein the topmost edge of the eyewear includes a left segment, a right segment, and a middle segment, each of which is oriented mediolaterally, the left segment and the right segment being aligned with each other at a first height and the middle segment being disposed at a higher second height to define a central raised portion.

Features, functions, and advantages may be achieved independently in various embodiments of the present disclosure, or may be combined in yet other embodiments, further details of which can be seen with reference to the following description and drawings.

DETAILED DESCRIPTION

Various aspects and examples of protective eyewear, as well as related methods, are described below and illustrated in the associated drawings. Unless otherwise specified, protective eyewear in accordance with the present teachings, and/or its various components, may contain at least one of the structures, components, functionalities, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

Referring to FIGS. 1 through 5, various exemplary embodiments are depicted comprising an eye protection device (e.g., goggle) 100 generally comprising a lens 102, mounted in a frame 104 and a strap 106 to hold the frame 104 and lens 102 securely against the user's face. Frame 104 is commonly made of a flexible polymer and includes an inner surface 108 that is shaped to conform to the user's face. This inner surface 108 is covered by a liner 110 such as a sheet of face foam to provide a comfortable seal against the user's face and help to absorb moisture such as perspiration.

The top area of inner surface 108 presses against the user's forehead area, the bottom area of inner surface 108 presses against the user's cheeks and across the user's nose, and the side areas of inner surface 108 press against the user's temples. Since the inner surface 108 is typically positioned behind the lens 102 and outer surface 118 of frame 104, inner surface 108 and liner 110 do not receive consistent airflow and thus may become a hot spot during exertion or in hot weather conditions that can cause discomfort and fogging issues.

Figure 1:
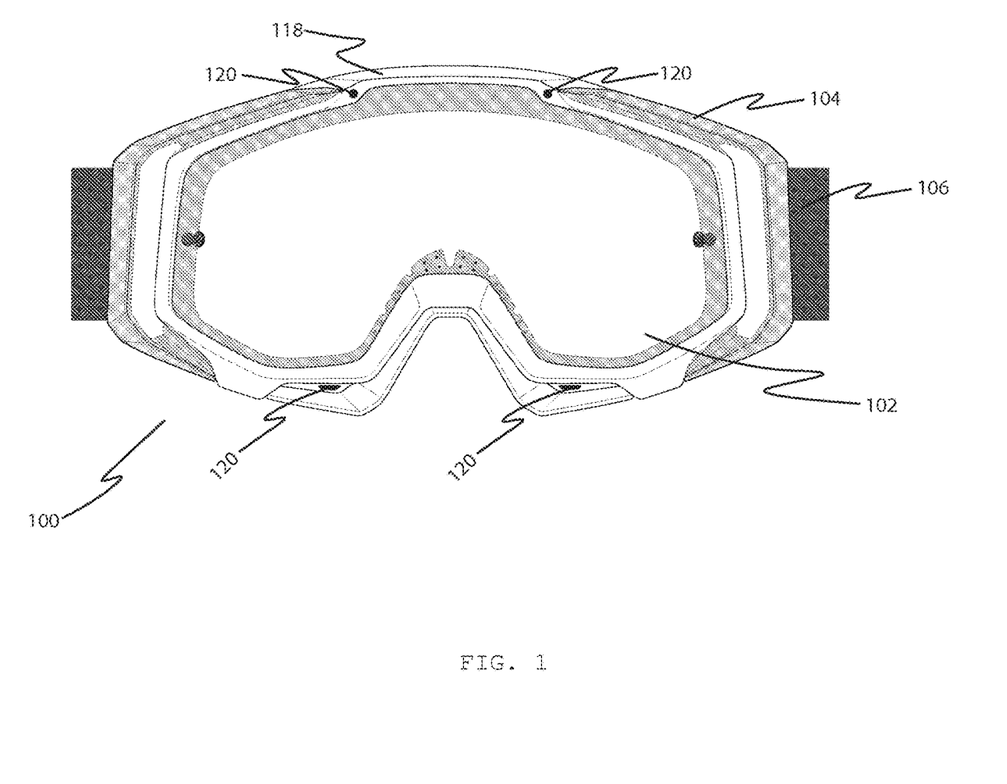
FIG. 1 is a diagram showing a front view of an embodiment of the present disclosure.
Figure 2:
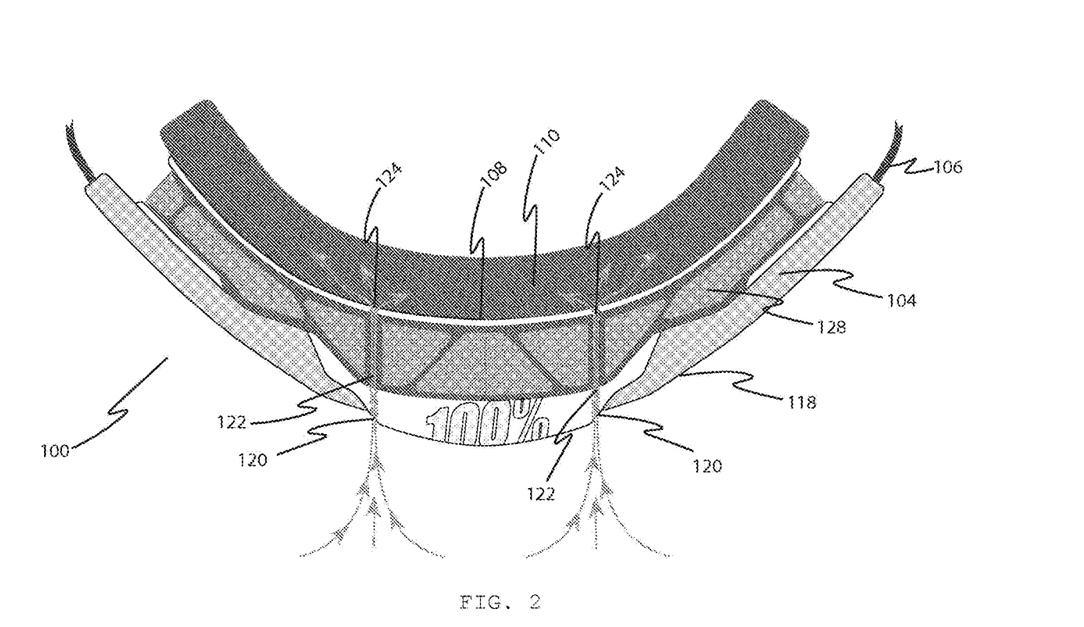
FIG. 2 is a diagram showing a top view of an embodiment of the present disclosure showing the air pathways through the frame of the goggle.
Figure 3:
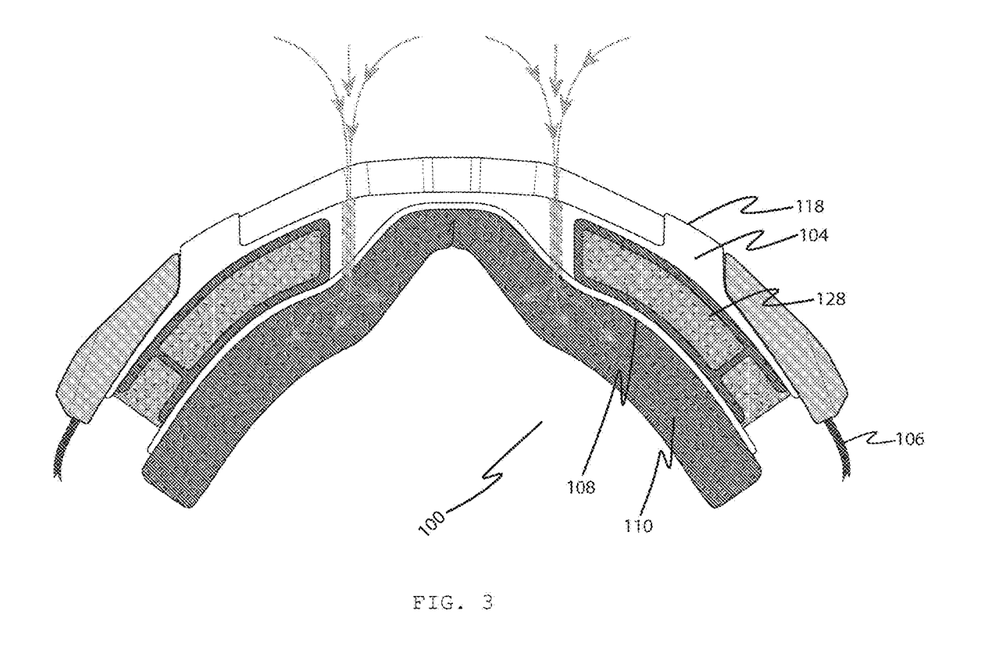
FIG. 3 is a diagram showing a bottom view of an embodiment of the present disclosure showing the air pathways through the frame of the goggle.
Figure 4:
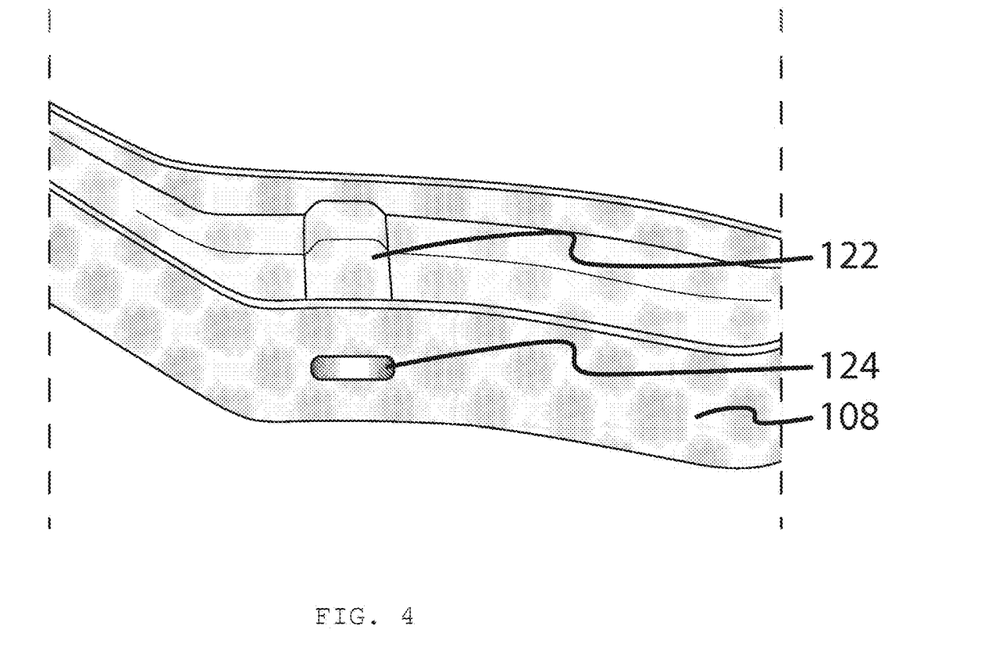
FIG. 4 is a diagram showing a section of the frame of an embodiment of the present disclosure.
Figure 5:
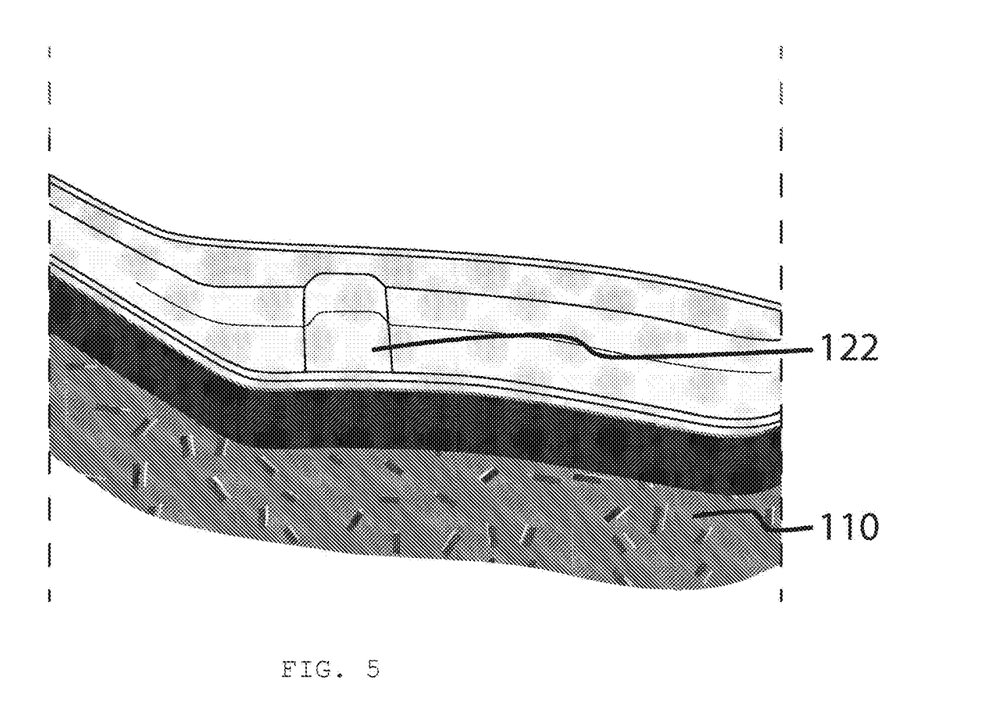
FIG. 5 is a diagram showing the same section of the frame of an embodiment of the present disclosure with foam positioned on the inner surface of the frame.

In an exemplary embodiment, one or more cooling vents are provided to manage airflow through the frame 104 so that it can be disbursed into the liner 110. In an exemplary embodiment, the cooling vents comprise first apertures 120 through the outer surface 118 of frame 104 that connect to channels 122 through the frame 104. These channels 122 connect to second apertures 124 through the inner surface 108. Thus, as illustrated in FIGS. 2 and 3, air flowing in through the first apertures 120 will pass along the channels 122 and through the second apertures 124, where it will be disbursed through the liner 110, cooling the liner 110 and the user's skin. Screens or other filters can be placed in the first apertures 120, channels 122, or second apertures 124 as appropriate.

Because these cooling vents provide a direct channel to the liner 110, the incoming airflow is not disbursed into the space between the lens 102 and the user's eyes and portion of their face that is within the areas circumscribed by inner surface 108. Venting into that space is typically managed by various types of direct vents 128 that allow air to flow in and out through the frame 104.

It will be readily understood that the size, shape, configuration, and orientation of the cooling vents disclosed herein can be varied while still practicing the disclosed principles. For example, goggles designed for use in dusty environments such as motocross racing may have first apertures of a relatively small size to reduce the risk of taking in large quantities of dust and dirt. Goggles designed for uses such as snowboarding or skiing may have larger apertures and channels, as dust is not a concern, but may utilize some type of closure mechanism to prevent cooling when the outside air is particularly cold. The shape and contours of the channels may also be varied to manage airflow through the frame.

Referring to FIGS. 6 through 13, various exemplary embodiments are depicted comprising an eye protection device (e.g., sunglasses) 200 generally comprising a lens 202, mounted in a frame 204 and temples 206 to hold the frame 204 and lens 202 securely near and/or against a user's face. Frame 204 may be made of a rigid or flexible polymer and may include an inner surface 208 that is generally shaped to conform to the user's face. In some embodiments, portions of inner surface 208 may be covered by a liner (e.g., similar to liner 110 in FIGS. 2-3 and 5) such as a sheet of foam to provide a comfortable seal against the users face and help to absorb moisture such as perspiration. For example, such a liner may cover the inner surface of a top portion of frame 204 and press against the user's forehead area to prevent sweat from entering the space between lens 202 and the user's face. In various embodiments, inner surface 208 may include side areas 272 configured to conform generally to the shape of a user's temples. Corresponding side portions 274 of frame 202 may be configured to join temples 206 to the rest of frame 202, and/or to couple to lens 202, for example, and may be implemented as fixed, hinged, and/or curved joints and/or engagement devices, as described herein.

Figure 6:
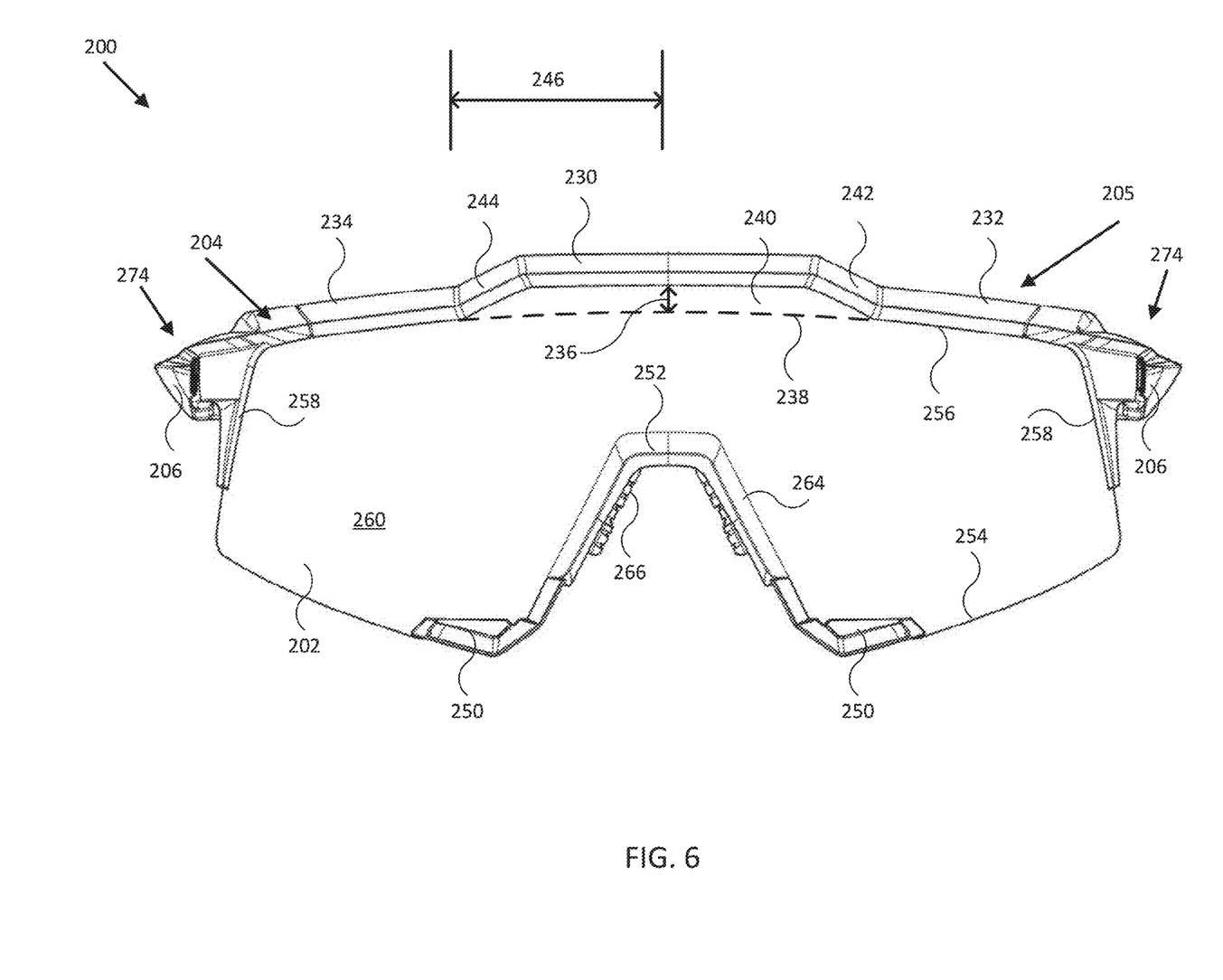
FIG. 6 is a diagram showing a front view of an embodiment of the present disclosure.

As shown in FIG. 6, frame 204 may in some embodiments include a central raised portion 230 disposed between left portion 232 and right portion 234 of a top portion of frame 202 (e.g., the portion of frame 204 substantially above lens 202). For example, central raised portion 230 may extend vertically a distance 236 above a substantially continuous profile (e.g., indicated by dashed line 238) corresponding to the left and right portions 232 and 234 of frame 204. In some embodiments, distance 236 may be equal to or greater than 3 mm, 3.5 mm, 4 mm, and/or other distances between 3 mm and 10 mm, for example, to allow for an extended vertical view for a user through central mesa portion 240 of lens 202. In various embodiments, central raised portion 230 may be coupled or joined to left and right portions 232 and 234 by corresponding left and right angled joints 242 and 244 formed from frame 204. In such embodiments, left and/or right angled joints 242 and/or 244 may be formed large enough to support apertures and/or channels to conduct airflow from an outer surface 205 of frame 204 to an inner surface 208 of frame 204 (e.g., see FIG. 9).

In FIG. 6, distance 246 illustrates the half width of central raised portion 230 roughly measuring the distance from the center line of central raised portion 230 (e.g., and frame 204) to a point where angled joint 244 deviates from profile 238. In some embodiments, distance 246 may be between approximately 20 mm and 60 mm, between approximately 30 mm and 60 mm, between approximately 40 mm and 60 mm, and/or other distances between approximately 20 mm and 80 mm, for example, to allow for a relatively wide extended vertical view for a user through central mesa portion 240 of lens 202. In further embodiments, distances 236 and/or 246, and/or a rake or angle of angled joints 242 and/or 244 may be adjusted to provide an increased or tailored extended vertical view for a particular eye spacing for a user, for example, yet still provide some protection from sunlight impinging upon left and/or right portions 232 and 234 of frame 204. Further, in some embodiments, frame 204 may include a relatively wide top surface 280 (e.g., see FIG. 10) to help block sunlight that would otherwise reach a user's eyes between a space between the top portion of frame 204 and a user's forehead.

Also shown in FIG. 6 are various features to provide adjustable airflow to a user wearing sunglasses 200, such as lens air scoops 250 disposed on either side of bridge 252 along a lower edge 254 of lens 202. Lens air scoops 250 may be formed from a relatively rigid or flexible polymer, for example, and/or from the same material utilized to form frame 204. In some embodiments, lens air scoops 250 may be glued or otherwise permanently fixed to lens 202, for example, and/or may include a hinged portion that may be utilized to open, close, or meter airflow through lens air scoops 250. In some embodiments, lens air scoops 250 may be removably coupled to lens 202, for example, and/or may be formed in conjunction with corresponding apertures formed through lens 202 and displaced away from lower edge 254 of lens 202.

Lens 202 may in some embodiments be a cylindrically or otherwise cut lens approximately 2 mm thick and including various coatings, fixed appendages, and/or other structures facilitating its use as a lens for sunglasses 200. In some embodiments, lens 202 may be between 1 mm and 3 mm thick to decrease weight, for example, or increase protection against ballistic and/or other objects that would otherwise harm the user. In addition to lower edge 254, lens 202 may include top edge 256, side edges 258, outer surface 260, and inner surface 262 (e.g., see FIG. 9). Edges 254, 256, and 258 may be configured to mate with channels, notches, adhesives, and/or other engagement devices associated with frame 204, lens air scoops 250, and/or nose pad 264, for example, so as to be removable and/or interchangeable with other lenses. In some embodiments, lens 202 may be selected from a range of profiles (e.g., height of lens 202) to reduce weight or increase airflow (e.g., with or without lens air scoops 250). As shown in FIG. 6, portions of lower edge 254 and side edges 258 may be free from any engagement device so as to reduce weight and provide for customized sizing to a user's cheek area, for example. Surfaces 260 and/or 262 may include one or more antireflective coatings, color coatings, filter coatings, hydrophobic coatings, anti-fog coatings, and/or other coatings to facilitate use of lens 202 in sunglasses 200. In some embodiments, surface 260 may support laser etching for product marketing and/or other optical features, and the material used to form lens 202 may be tinted or otherwise selected for a particular desired color. More generally, lens 202 may be made of one or more materials that are partially or totally absorptive or reflective of one or more types of ultraviolet radiation, for example, and lens 202 may be configured (e.g., through choice of materials, formation methods, polishing methods, coating application methods, and/or other configuration choices) to provide clarity of view for a user in any of a variety of different environmental conditions (e.g., desert, sea, mountain, summer, winter, and/or other environmental conditions).

Additionally shown in FIG. 6 is nose pad 264, which in some embodiments may include grip portion 266, that is configured to help secure sunglasses 200 to a user's face. For example, nose pad 264 may be configured to be positioned between bridge 252 of the eye protection device and the user's nose. Nose pad and/or grip portion may be implemented from a relatively rigid or flexible polymer or material, for example, and in some specific embodiments, grip portion 266 may be formed from and/or coated with Megol® rubber or other relatively flexible and soft material to help comfortably secure sunglasses 200 to the user's face. In some embodiments, nose pad 264 may be glued or otherwise permanently fixed to bridge 252 and/or lower edge 254 of lens 202, for example. In some embodiments, nose pad 264 may be removably coupled to lens 202 so as to be interchangeable with other nose pads, such as nose pads designed to fit a particular user's nose or comfort level, or to provide additional protection against objects that would otherwise strike a user's face or nose.

Figure 7:
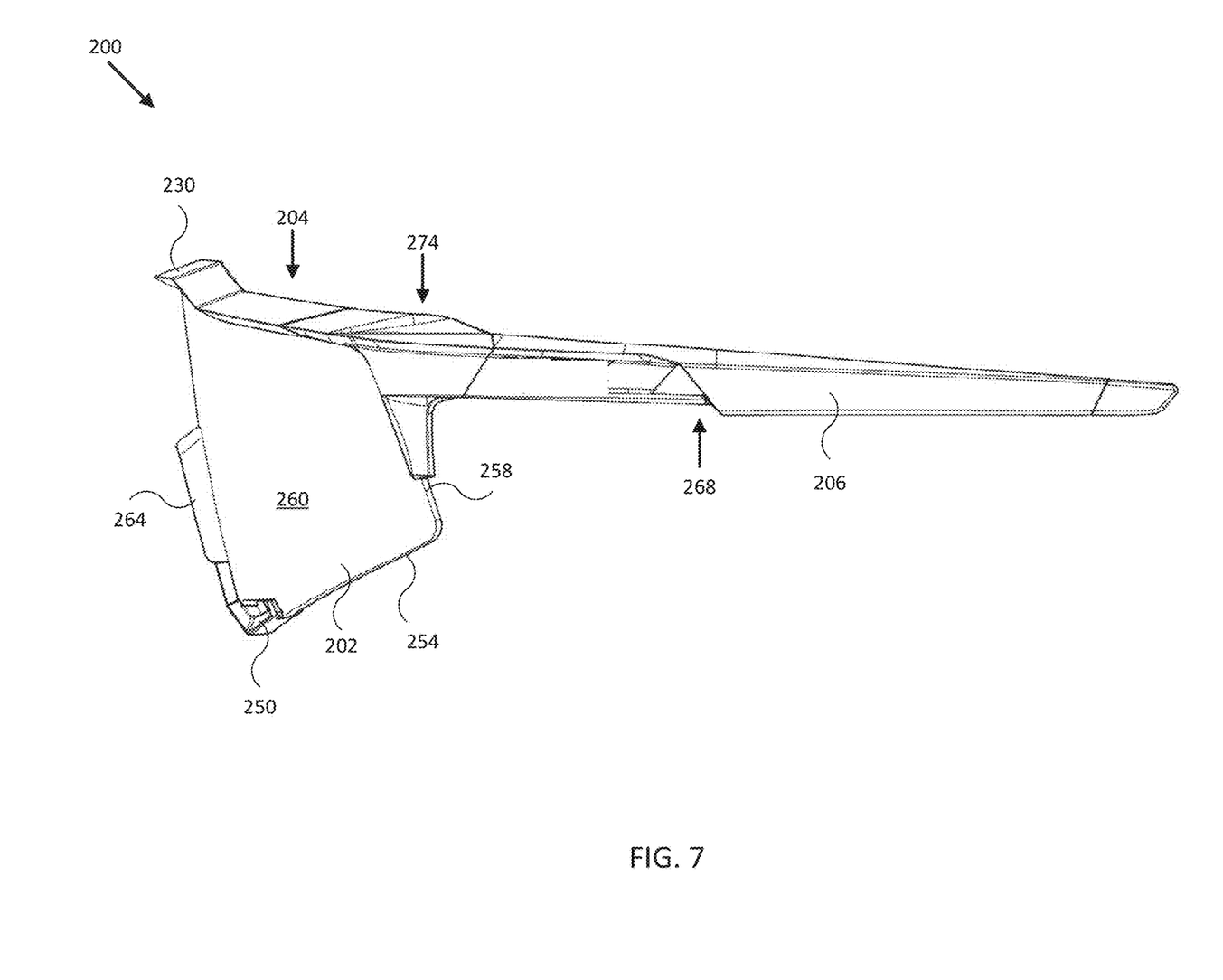
FIG. 7 is a diagram showing a side view of an embodiment of the present disclosure.
Figure 8:
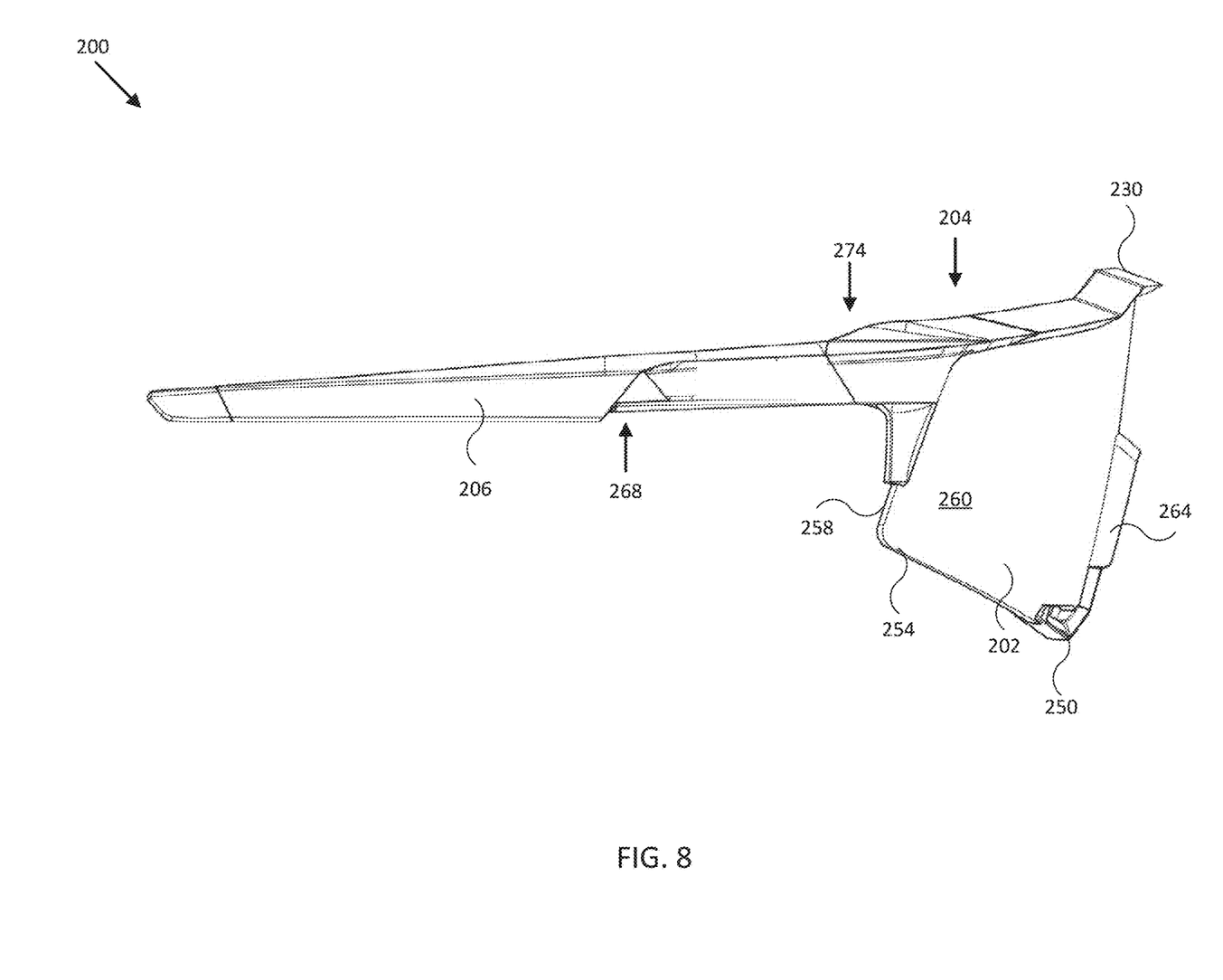
FIG. 8 is a diagram showing a side view of an embodiment of the present disclosure.
Figure 9:
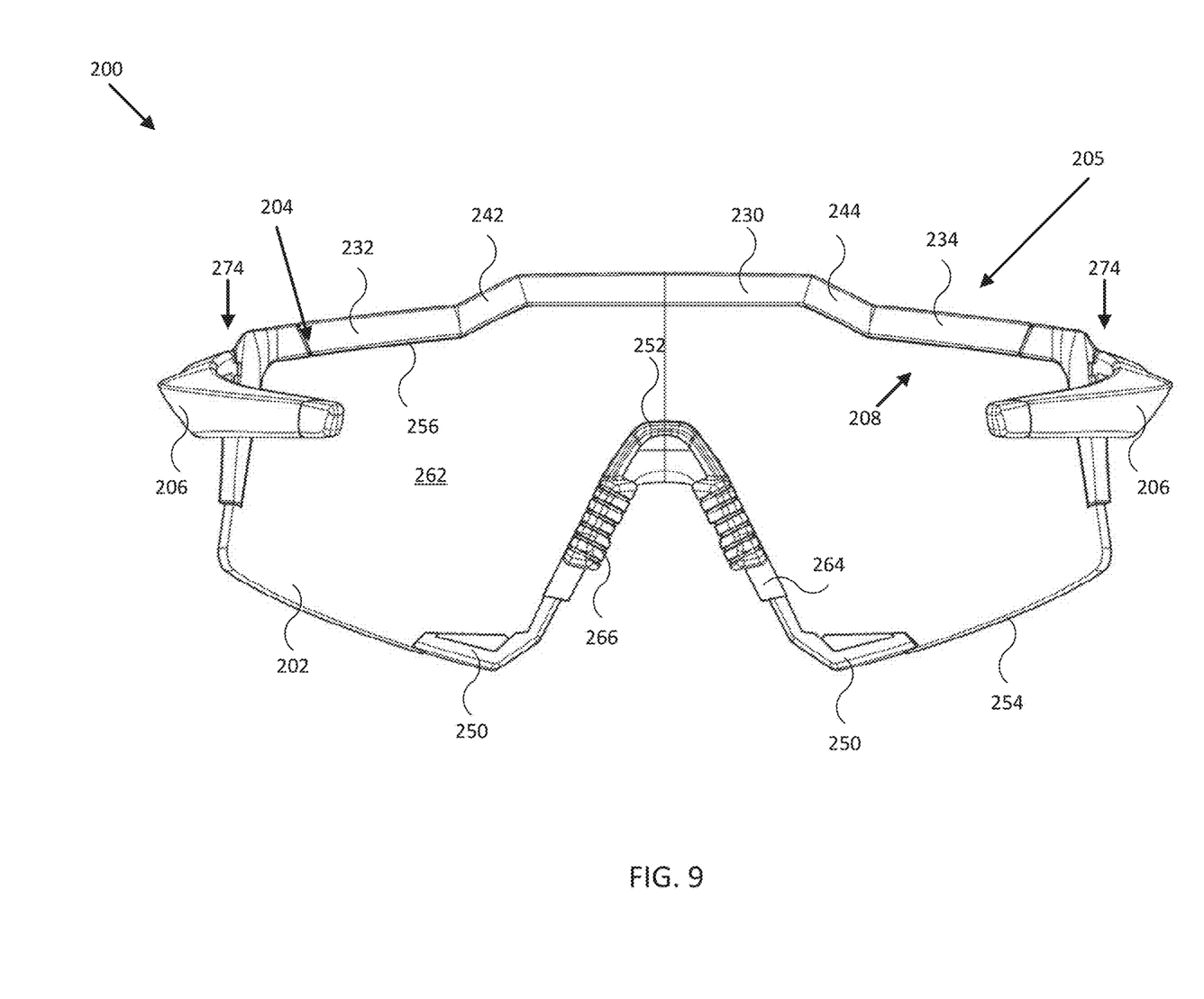
FIG. 9 is a diagram showing a rear view of an embodiment of the present disclosure.
Figure 10:
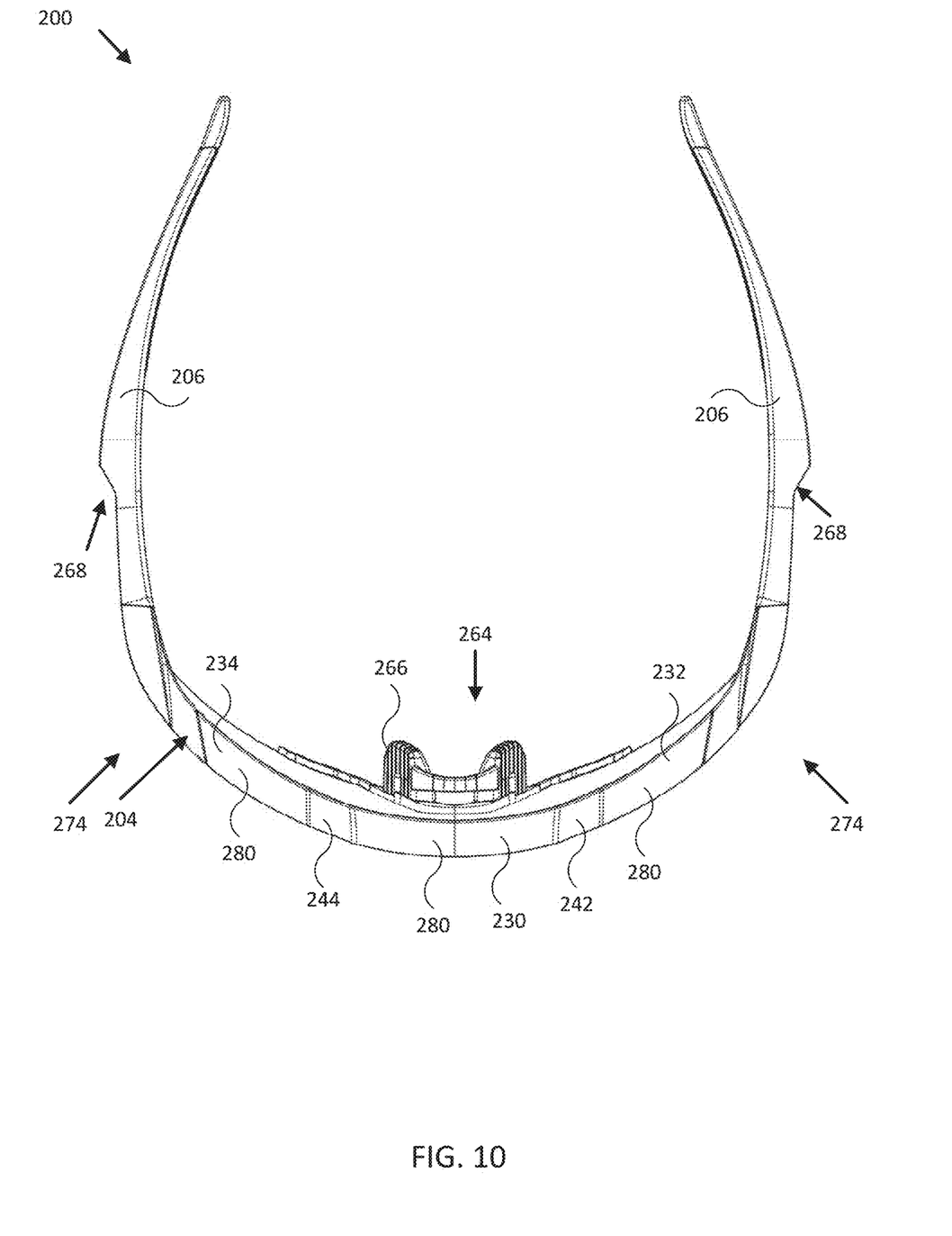
FIG. 10 is a diagram showing a top view of an embodiment of the present disclosure.
Figure 11:
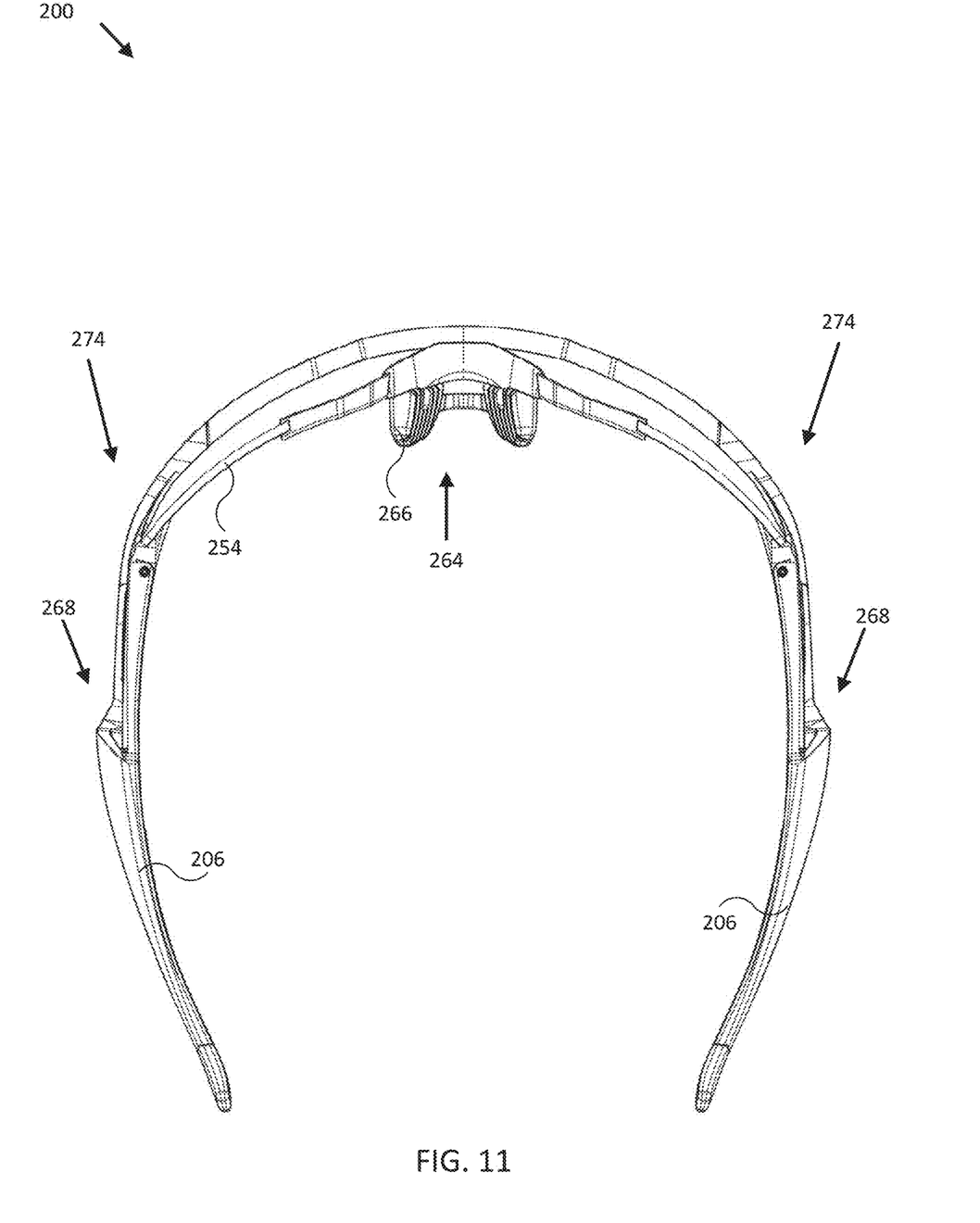
FIG. 11 is a diagram showing a bottom view of an embodiment of the present disclosure.

As shown in FIG. 7, in some embodiments, temples 206 of sunglasses 200 may include one or more temple air scoops 268 formed within temples 206. Temple air scoops 268 may be formed as scoop-like apertures and channels extending from an outer surface of temple 206 to an inner surface of temple 206 that is typically close to or in contact with a user's temple area. As shown, temple air scoops 268 may be configured to scoop air traveling from the front of sunglasses 200 toward the rear of sunglasses 200 generally horizontally along temple 206, for example, and deliver it to the user's temple area so as to increase airflow and decrease discomfort due to heat and/or sweat buildup between frame 204 and the user's head.

Figure 12:
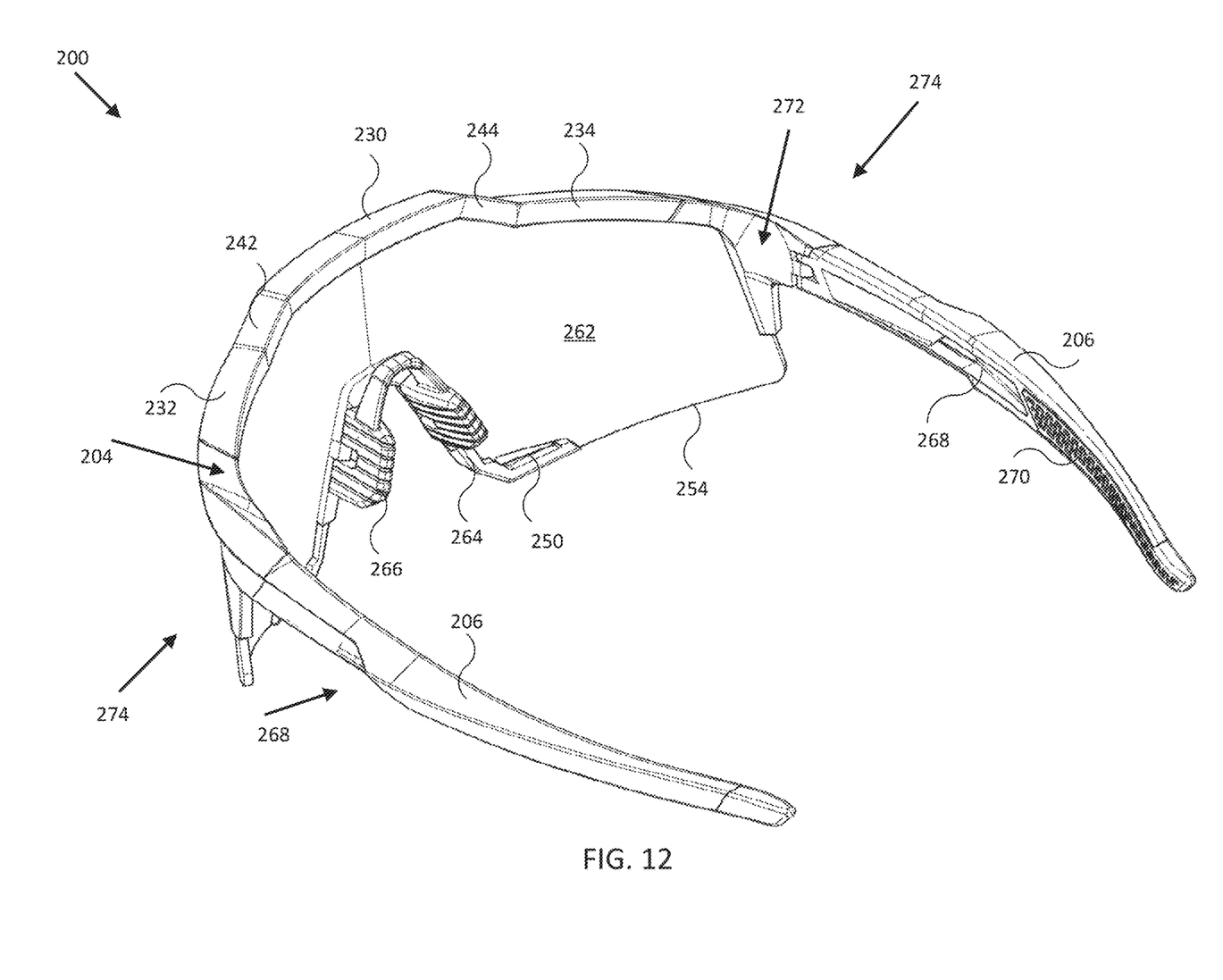
FIG. 12 is a diagram showing an orthographic view of an embodiment of the present disclosure.
Figure 13:
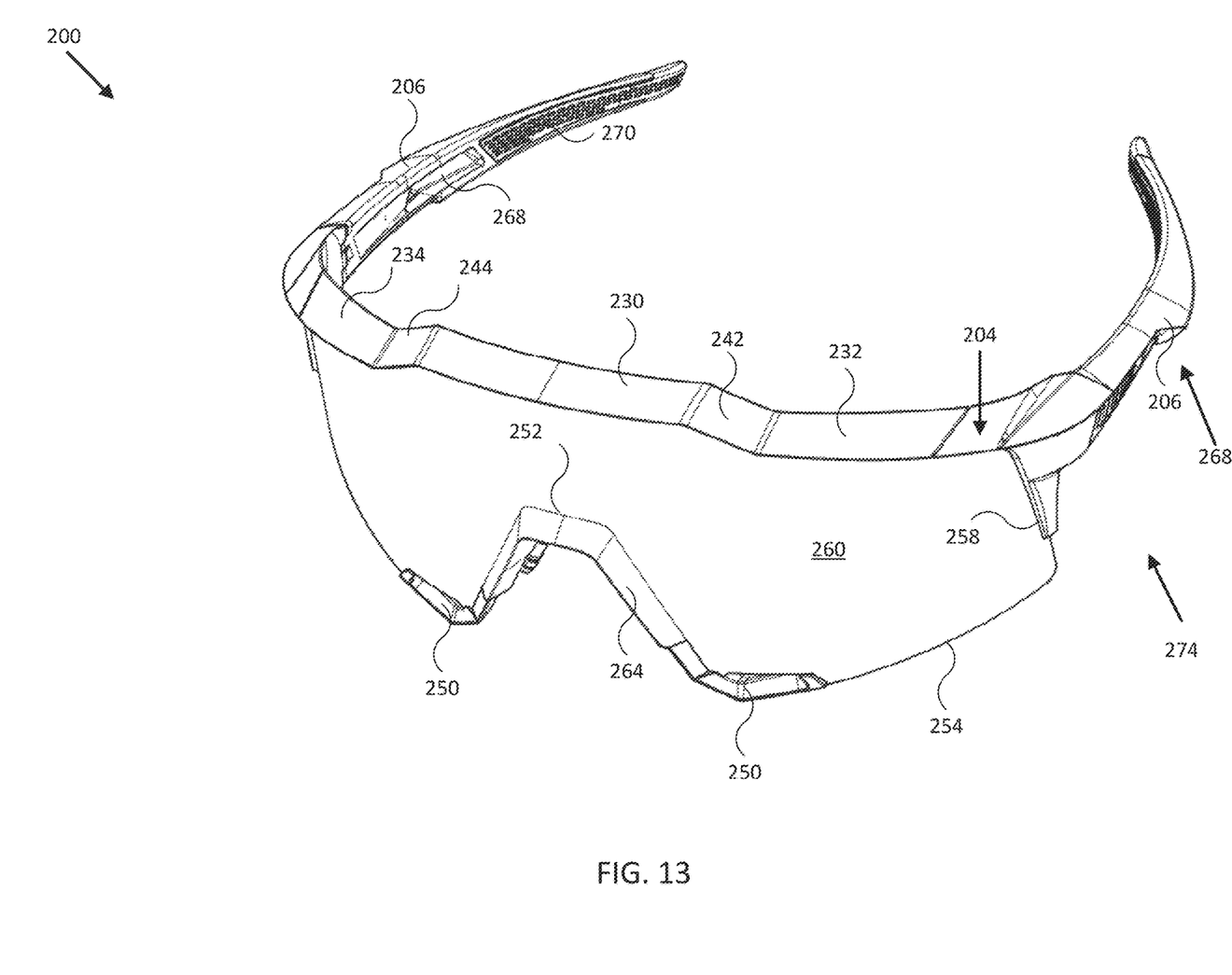
FIG. 13 is a diagram showing an orthographic view of an embodiment of the present disclosure.

As shown in FIGS. 12 and 13, the general wraparound design of sunglasses 200 (e.g., and/or of lens 202 and/or frame 204) facilitates securing sunglasses 200 to a user's face while providing protection from almost all angles of sunlight and/or objects that might otherwise harm a user's eyes and/or face. For example, temples 206 may include temple grip portions 270 to help comfortably secure sunglasses 200 to a user, such as without interfering with a helmet. In some embodiments, temple grip portions 270 may be formed in the same manner and/or using the same material used to form nose pad grip portions 266. Moreover, the wraparound design may be configured to provide ample space between lens 202 and a user's face, which can help increase airflow and reduce a chance of fogging/condensation. In particular, the horizontal and/or vertical curvature (e.g., or absence of curvature) of lens 202 (e.g., and/or frame 204), as shown in FIGS. 12 and 13, may provide configurable/selectable space between lens 202 and a user's face, for example, through use of the interchangeable nature of lens 202.

A typical method of use may include steps of assembly of sunglasses 200 from component parts, such as before or after testing a particular assembly for fit, adequate cooling, adequate view, and/or selecting particular components for a specific expected use, such as motocross, fishing, running, and/or other uses. For example, a first step may include inspecting frame 204 for a particular size and shape of central raised portion 230, for example, and narrowing a selection of lenses to only those that will fit frame 204. Next, a particular lens 202 may be selected according to a desired level of tint, a particular coating, a particular profile (e.g., size and/or coverage), a particular curvature, and/or other characteristics disclosed herein. Then, the selected lens may be attached to frame 204 (e.g., to top portion 205 and side portions 274 of frame 204) through use of channels and/or other engagement devices or structures of frame 204 and/or lens 202. In some embodiments, a particular lens 202 may come with attached lens air scoops 250. In some embodiments, specific lens air scoops may be selected and attached to lens 202. Next, a particular nose pad 264 may be selected for comfort, fit, and/or other desire characteristics described herein. Then, the selected nose pad 264 may be attached to lens 202 at bridge 252 and/or along lower edge 254, as shown in FIGS. 6-13. Once assembly is complete sunglasses 200 may be placed around a user's face, temple, and/or head to secure sunglasses 200 to the user. A user wearing sunglasses 200 may then participate in an activity and sunglasses 200 may provide an extended vertical view with which to see, for example, a road or vertical periphery while riding a bicycle or motorcycle and/or otherwise engaging in a sport.

CONCLUSION

In this disclosure, one or more publications, patents, and/or patent applications may be incorporated by reference.

However, such material is only incorporated to the extent that no conflict exists between the incorporated material and the statements and drawings set forth herein. In the event of any such conflict, including any conflict in terminology, the present disclosure is controlling.

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

The invention claimed is:

1. Protective eyewear, comprising:
   an eyewear frame including a left segment extending from a left pivotable temple and a right segment extending from a right pivotable temple; and
   a lens coupled directly to lower edges of the left and right segments, the lens being unitary from a left side to a right side of a nose bridge of the eyewear, such that the lens is configured to cover both eyes of a user when worn;
   wherein an uppermost profile of the eyewear includes a discrete central raised portion extending upward from the left and right segments of the frame.

2. The protective eyewear of claim 1, wherein the central raised portion has a generally trapezoidal shape.

3. The protective eyewear of claim 1, wherein no other portion of the eyewear frame obstructs the central raised portion when viewed from a front or a back of the lens.

4. The protective eyewear of claim 1, wherein the left and right segments of the frame are aligned with each other across the central raised portion.

5. The protective eyewear of claim 1, wherein the uppermost profile of the eyewear is defined by a topmost frame member extending from the left pivotable temple to the right pivotable temple.

6. The protective eyewear of claim 5, wherein an upper edge of the lens is in continuous contact with a lower surface of the topmost frame member across a width of the frame.

7. The protective eyewear of claim 1, wherein the lens fills the central raised portion.

8. The protective eyewear of claim 1, wherein the left pivotable temple and the right pivotable temple each comprise a respective channel extending from a respective first aperture formed on a lateral surface of the corresponding pivotable temple to a respective second aperture formed on a medial surface of the corresponding pivotable temple.

9. The protective eyewear of claim 8, wherein the left and right pivotable temples are coupled to the frame segments at respective connection points, and each of the first apertures is disposed between the corresponding connection point and the corresponding second aperture, wherein each of the first apertures is formed on a forward-facing portion of the corresponding lateral surface.

10. The protective eyewear of claim 1, further comprising at least one airflow passage at least partially defined by the lower edge of the lens, the airflow passage extending from a front surface of the eyewear to a rear surface of the eyewear.

11. The protective eyewear of claim 10, wherein the at least one airflow passage is defined between the lower edge of the lens and a lateral portion of the nose bridge of the eyewear extending below the lower edge of the lens.

12. Protective eyewear, comprising:
    a frame and a lens collectively forming a topmost edge of the eyewear extending from a left pivotable temple to a right pivotable temple;
    wherein the lens is unitary from a left side to a right side of a nose bridge of the eyewear, such that the lens is configured to cover both eyes of a user when worn; and
    wherein the topmost edge of the eyewear includes a left segment, a right segment, and a middle segment, each of which is oriented mediolaterally, the left segment and the right segment being aligned with each other at a first height and the middle segment being disposed at a higher second height to define a central raised portion.

13. The eyewear of claim 12, wherein the lens fills a space defined by the central raised portion.

14. The eyewear of claim 12, wherein the frame extends continuously along the topmost edge.

15. The eyewear of claim 14, wherein an upper edge of the lens is in continuous contact with a lower surface of the frame along the topmost edge of the eyewear.

16. The protective eyewear of claim 12, wherein a space defined by the central raised portion has a generally trapezoidal perimeter.

17. The protective eyewear of claim 12, wherein no other portion of the eyewear frame obstructs the central raised portion when viewed from a front or a back of the lens.

18. The protective eyewear of claim 12, wherein no other portion of the protective eyewear extends above the middle segment of the topmost edge when worn.

* * * * *